（12） United States Patent
Kingscott

(10) Patent No.: US 10,555,700 B2
(45) Date of Patent: Feb. 11, 2020

(54) COMBINED OPTICAL SENSOR FOR AUDIO AND PULSE OXIMETRY SYSTEM AND METHOD

(71) Applicant: BRAGI GmbH, München (DE)

(72) Inventor: Lisa Kingscott, München (DE)

(73) Assignee: BRAGI GmbH, München (DE)

( * ) Notice: Subject to any disclaimer, the term of this patent is extended or adjusted under 35 U.S.C. 154(b) by 155 days.

(21) Appl. No.: 15/637,244

(22) Filed: Jun. 29, 2017

(65) Prior Publication Data

US 2018/0008198 A1 Jan. 11, 2018

Related U.S. Application Data

(60) Provisional application No. 62/359,027, filed on Jul. 6, 2016.

(51) Int. Cl.
*A61B 5/00* (2006.01)
*A61B 5/1455* (2006.01)

(52) U.S. Cl.
CPC .......... *A61B 5/6815* (2013.01); *A61B 5/1455* (2013.01); *A61B 5/683* (2013.01); *A61B 5/7207* (2013.01); *A61B 5/7221* (2013.01); *A61B 5/7235* (2013.01); *A61B 5/7415* (2013.01)

(58) Field of Classification Search
CPC ..... A61B 5/1455; A61B 5/683; A61B 5/6815; A61B 5/7415; A61B 5/7235; A61B 5/7207; A61B 5/7221
See application file for complete search history.

(56) References Cited

U.S. PATENT DOCUMENTS

| 2,325,590 A | 8/1943 | Carlisle et al. |
| 2,430,229 A | 11/1947 | Kelsey |
| 3,047,089 A | 7/1962 | Zwislocki |
| D208,784 S | 10/1967 | Sanzone |

(Continued)

FOREIGN PATENT DOCUMENTS

| CN | 204244472 U | 4/2015 |
| CN | 104683519 A | 6/2015 |

(Continued)

OTHER PUBLICATIONS

Akkermans, "Acoustic Ear Recognition for Person Identification", Automatic Identification Advanced Technologies, 2005 pp. 219-223.

(Continued)

*Primary Examiner* — Max F Hindenburg
(74) *Attorney, Agent, or Firm* — Goodhue, Coleman & Owens, P.C.

(57) ABSTRACT

A system includes at least one earpiece, wherein each earpiece comprises an earpiece housing, an optical source operatively connected to the earpiece housing, wherein the optical source is configured to emit light toward an ear surface, an optical sensor operatively connected to the earpiece housing, wherein the optical sensor is configured to receive reflected light from the ear surface, and at least one processor disposed within at least one earpiece and operatively connected to the optical source and the optical sensor, wherein the at least one processor is configured to separate the pulse oximetry signals from the audio signals in the reflected light detected by the optical sensor.

12 Claims, 6 Drawing Sheets

(56) References Cited

U.S. PATENT DOCUMENTS

| | | |
|---|---|---|
| 3,586,794 A | 6/1971 | Michaelis |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| D601,134 S | 9/2009 | Elabidi et al. |
| 7,825,626 B2 | 11/2010 | Kozisek |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| D666,581 S | 9/2012 | Perez |
| 8,300,864 B2 | 10/2012 | Müllenborn et al. |
| 8,406,448 B2 | 3/2013 | Lin et al. |
| 8,436,780 B2 | 5/2013 | Schantz et al. |
| D687,021 S | 7/2013 | Yuen |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg et al. |
| D788,079 S | 5/2017 | Son et al. |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |

(56) References Cited

U.S. PATENT DOCUMENTS

| | | |
|---|---|---|
| 2006/0029246 A1 | 2/2006 | Boesen |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2008/0076972 A1 | 3/2008 | Dorogusker et al. |
| 2008/0090622 A1 | 4/2008 | Kim et al. |
| 2008/0146890 A1 | 6/2008 | LeBoeuf et al. |
| 2008/0254780 A1 | 10/2008 | Kuhl et al. |
| 2008/0255430 A1 | 10/2008 | Alexandersson et al. |
| 2009/0003620 A1 | 1/2009 | McKillop et al. |
| 2009/0017881 A1 | 1/2009 | Madrigal |
| 2009/0073070 A1 | 3/2009 | Rofougaran |
| 2009/0097689 A1 | 4/2009 | Prest et al. |
| 2009/0105548 A1 | 4/2009 | Bart |
| 2009/0191920 A1 | 7/2009 | Regen et al. |
| 2009/0245559 A1 | 10/2009 | Boltyenkov et al. |
| 2009/0296968 A1 | 12/2009 | Wu et al. |
| 2010/0033313 A1 | 2/2010 | Keady et al. |
| 2010/0203831 A1 | 8/2010 | Muth |
| 2010/0210212 A1 | 8/2010 | Sato |
| 2010/0320961 A1 | 12/2010 | Castillo et al. |
| 2011/0286615 A1 | 11/2011 | Dlodort et al. |
| 2012/0057740 A1 | 3/2012 | Rosal |
| 2013/0316642 A1 | 11/2013 | Newham |
| 2013/0346168 A1 | 12/2013 | Zhou et al. |
| 2014/0058220 A1* | 2/2014 | LeBoeuf ............ A61B 5/0059 600/301 |
| 2014/0072146 A1 | 3/2014 | Itkin et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0163771 A1 | 6/2014 | Demeniuk |
| 2014/0185828 A1 | 7/2014 | Helbling |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0348367 A1 | 11/2014 | Vavrus et al. |
| 2015/0028996 A1 | 1/2015 | Agrafioti et al. |
| 2015/0110587 A1 | 4/2015 | Hori |
| 2015/0148989 A1 | 5/2015 | Cooper et al. |
| 2015/0245127 A1 | 8/2015 | Shaffer |
| 2016/0033280 A1 | 2/2016 | Moore et al. |
| 2016/0072558 A1 | 3/2016 | Hirsch et al. |
| 2016/0073189 A1 | 3/2016 | Lindén et al. |
| 2016/0125892 A1 | 5/2016 | Bowen et al. |
| 2016/0360350 A1 | 12/2016 | Watson et al. |
| 2017/0078780 A1 | 3/2017 | Qian et al. |
| 2017/0111726 A1 | 4/2017 | Martin et al. |
| 2017/0155992 A1 | 6/2017 | Perianu et al. |

FOREIGN PATENT DOCUMENTS

| | | |
|---|---|---|
| CN | 104837094 A | 8/2015 |
| EP | 1469659 A1 | 10/2004 |
| EP | 1017252 A3 | 5/2006 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014043179 A2 | 3/2014 |
| WO | 2014046602 A1 | 3/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |

OTHER PUBLICATIONS

Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI is on Facebook (2014).
BRAGI Update—Arrival of Prototype Chassis Parts —More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, on Track(May 16, 2015).
BRAGI Update—Beta2 Production and Factory Line(Aug. 20, 2015).
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces A Health +0 Mobility Concept for Wellness in Mobility", Fountain Valley, Califorra (2017).
Last Push Before the Kickstarter Campaign Ends on Monday 4pm CET (Mar. 28, 2014).

(56) References Cited

OTHER PUBLICATIONS

Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).

Staab, Wayne J., et al., "A One-Size Disposable Hearing Aid is Introduced", The Hearing Journal 53(4):36-41) Apr. 2000.

Stretchgoal—Its Your Dash (Feb. 14, 2014).

Stretchgoal—The Carrying Case for the Dash (Feb. 12, 2014).

Stretchgoal—Windows Phone Support (Feb. 17, 2014).

The Dash + The Charging Case & The BRAGI News (Feb. 21, 2014).

The Dash—A Word From Our Software, Mechanical and Acoustics Team + An Update (Mar. 11, 2014).

Update From BRAGI—$3,000,000—Yipee (Mar. 22, 2014).

\* cited by examiner

COMBINED OPTICAL SENSOR FOR AUDIO AND PULSE OXIMETRY SYSTEM AND METHOD

PRIORITY STATEMENT

This application claims priority to U.S. Provisional Patent Application 62/359,027, filed on Jul. 6, 2016, and entitled Combined Optical Sensor for Audio and Pulse Oximetry System and Method, hereby incorporated by reference in its entirety.

FIELD OF THE INVENTION

The present invention relates to wearable devices. More particularly, but not exclusively, the present invention relates to earpieces.

BACKGROUND

The earpiece holds great promise as a wearable device. However, one of the challenges with incorporating various functionality into an earpiece is the relatively small space. What is needed is technology which allows for improved functionality for an earpiece but reduces the amount of space required.

For example, currently, two separate sensor assemblies are required for the proper determination of pulse oximetry and audio detection in an earpiece device. This means that the user must wear a device that is large enough to accommodate both of these sensors. This causes problems with design and usability, as well as creating further issues with costs of the materials required to provide an adequate audio and pulse oximetry signal for processing. In addition, further work is required in order to provide shielding from other components of the device, due to the space available in comparison to the amount of electronic components needed to support each input modality. What is needed is a new combined optical sensor for detecting both audio signals as well as pulse oximetry.

SUMMARY

Therefore, it is a primary object, feature, or advantage of the present invention to improve over the state of the art.

It is a further object, feature, or advantage of the present invention to combine the reception of audio signals and oxygen saturation data onto a single sensor.

It is a still further object, feature, or advantage of the present invention to separate the audio signals and the oxygen saturation data using signal processing techniques.

It is another object, feature, or advantage to reduce the number of key components.

Another object, feature, or advantage is to enhance ability to incorporate other sensor arrays due to enhanced space availability.

Yet another object, feature, or advantage is to reduce power requirements due to the reduction in the number of power intensive components.

A further object, feature, or advantage is allow signal processing to provide more information about blood flow in a studied area.

A still further object, feature, or advantage is to provide new opportunities to enhance amount and variety of sensed data.

One or more of these and/or other objects, features, or advantages will become apparent from the specification and claims that follow. No single embodiment need include each and every object, feature, or advantage as different embodiments may achieve different objects, features, and advantages.

A new and novel system combines the optical sensor for both the detection of high quality audio signals as well as the accurate detection of pulse oximetry from the earpiece. This new system may include a high quality optical source that provides the emitted light directed at the skin, cartilage and bone of the external ear. An optical sensor is utilized to detect the reflected signals from the skin, bone and cartilage of the external ear. The received signal may include both low frequency pulse oximetry signals as well as higher frequency audio signals. In this fashion, the combined sensor is able to receive audio signals emanated from the body and transmitted through bone and soft tissues, as well as the pulse rate and oxygen saturation from reflected light from blood. Signal processing then is used to detect and segregate the two signals. Transmission of the processed information is then possible using various schemes including wired or wireless transmission methods. This has the advantage of detecting multiple signals using a single sensor.

According to one aspect, a system includes at least one earpiece, wherein each earpiece comprises an earpiece housing, an optical source operatively connected to the earpiece housing, wherein the optical source is configured to emit light toward an ear surface, an optical sensor operatively connected to the earpiece housing, wherein the optical sensor is configured to receive reflected light from the ear surface, and at least one processor disposed within at least one earpiece and operatively connected to the optical source and the optical sensor, wherein the at least one processor is configured to separate the pulse oximetry signals from the audio signals in the reflected light detected by the optical sensor. The at least one processor may be further configured to determine an oxygen saturation level from the pulse oximetry signals. The at least one processor may apply a filter to separate the pulse oximetry signals from the audio signals, the audio signals centered at frequency higher than the pulse oximetry signals. The at least one earpiece may include a set of earpieces. The optical source may be a laser. The ear surface may be an outer ear surface or an inner ear surface. The at least one processor may be further configured to determine bone vibration measurements from the audio signals. The at least one processor may be further configured to interpret the bone vibrations measurements and to determine voice input from a user of the wireless earpiece. The method may further include reconfiguring the at least one processor using the voice input.

According to another aspect, a method includes emitting, via an optical source of a wireless earpiece, light toward an ear surface, receiving, via an optical sensor of the wireless earpiece, a reflected light signal from the ear surface, separating, via at least one processor of the wireless earpiece, audio signals from pulse oximetry signals within the reflected light signal, and determining, via the at least one processor of the wireless earpiece, an oxygen saturation level from the reflected light.

DETAILED DESCRIPTION

Figure 1:
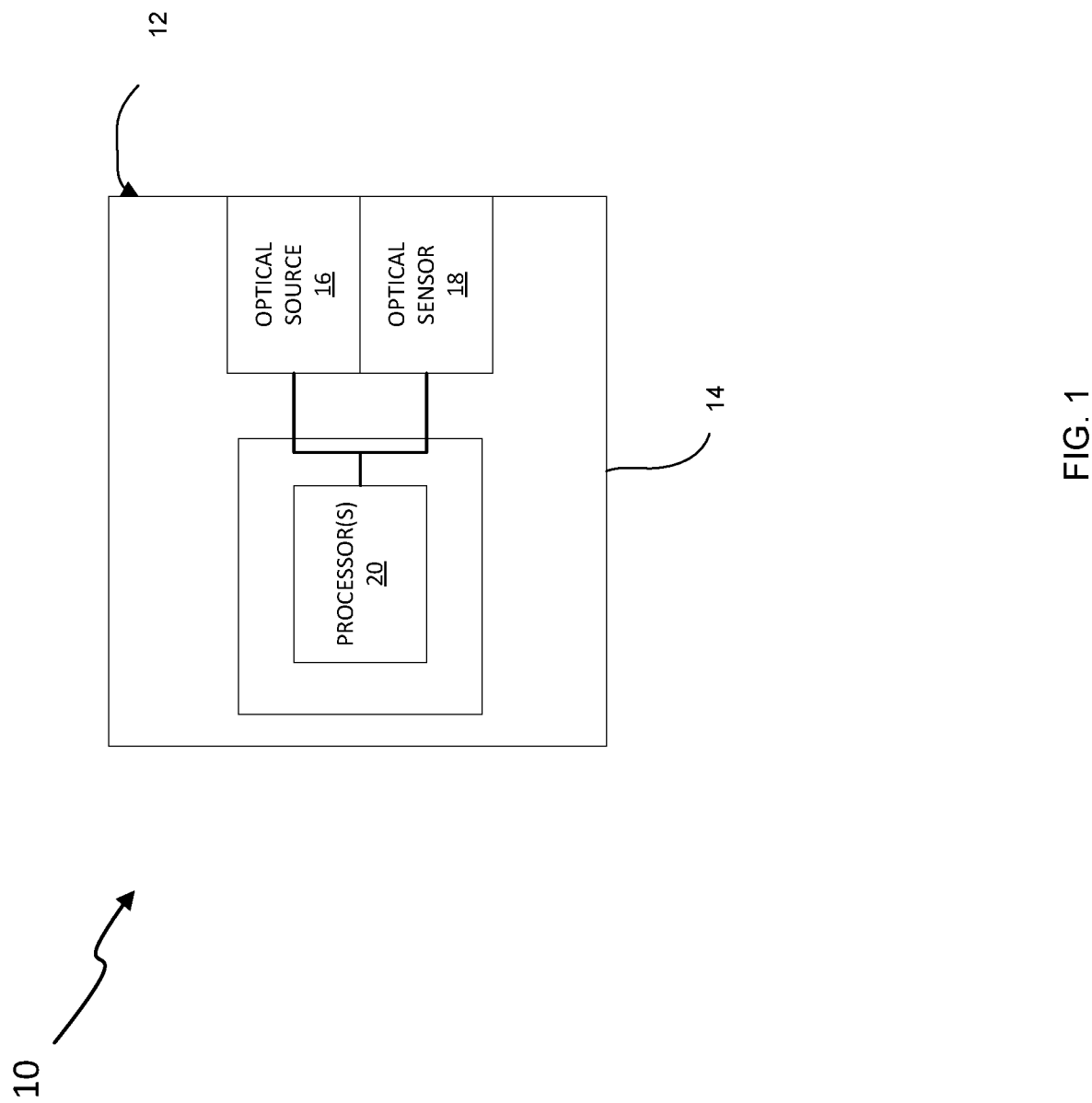
FIG. 1 is a block diagram of one embodiment of the system.

FIG. 1 illustrates a block diagram of the system 10 including one or more earpieces 12, with each earpiece comprising an earpiece housing 14, an optical source 16 operatively connected to an earpiece housing 14, an optical sensor 18 operatively connected to an earpiece housing 14, and one or more processors 20 operatively connected to the optical source 16 and the optical sensor 18. The optical source 16 is configured to emit light toward an ear surface, which may be on the outside or the inside of a user's body. Instead of an optical source, other types of electromagnetic wave sources may be used which emit any type of electromagnetic wave capable of reflecting off of ear tissue. For example, a radio wave may be used instead of a light source, as radio waves partially reflect off of living tissue. The optical sensor 18 operatively connected to the earpiece housing 14 is configured to receive reflected light from the ear surface. The reflected light may contain audio signals as well as pulse oximetry signals. The audio signals may also be used to modify an operational state of the earpiece 12. The reflected light may be received intermittently by the optical sensor 18 or may be received continuously depending on the operation of the optical source 16. One or more processors 20 are configured to separate the audio signals and the pulse oximetry signals from the reflected light. The audio may then be used for any number of purposes including receiving voice input from a user and the pulse oximetry signals may be used to determine an oxygen saturation level. The reflected light data may be received continuously or discretely, and the processors 20 do not need to use every bit of data in determining an oxygen saturation level. The separation of the signals may be performed in any number of ways including through the use of filtering of the reflected signal. The reflected signal may include both low frequency pulse oximetry signals as well as higher frequency, thus high pass filters and/or low pass filters may be used.

Figure 2:
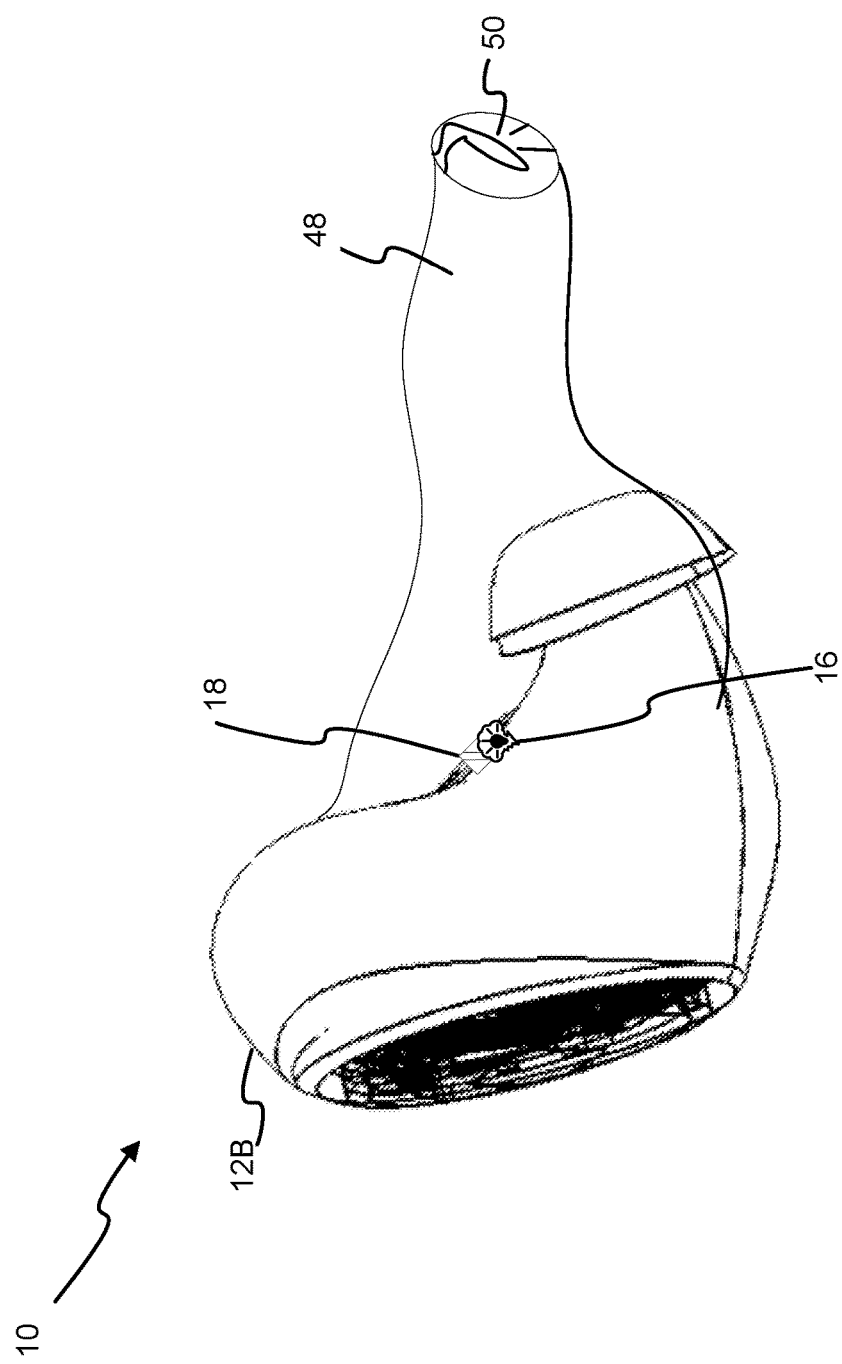
FIG. 2 illustrates a side view of a right earpiece and the functional relationships of the right earpieces components a user.

FIG. 2 shows a right earpiece 12B inserted into a user's ear having an optical source 16 and an optical sensor 18. The right earpiece 12B may be an ear bud style device configured to fit comfortably within a user's ear canal 48 so as to both minimize the amount of external sound reaching the user's ear canal 48 and to facilitate the transmission of sounds to a user's tympanic membrane 50. Ideally, the ear surface will be the inside of a user's ear canal 48, but the light may be directed at any surface within the user's ear or proximate thereto. Positioning the optical source 16 and the optical sensor 18 inside the user's ear canal 48 has three distinct advantages. One, the inside of the user's ear canal 48 contains little if no external light, allowing easier and more accurate measurements by the optical sensor 18. Two, the inside of the user's ear canal 48 allows ready access to areas suitable for oxygen saturation measurements. Three, the distance between the optical source 16 and the ear surface in the user's ear canal 48 is approximately the same for each prospective user and ideally both the optical source 16 and the optical sensor 18 touch the ear surface 26 directly, allowing for relatively accurate oxygen saturation calculations.

Figure 3:
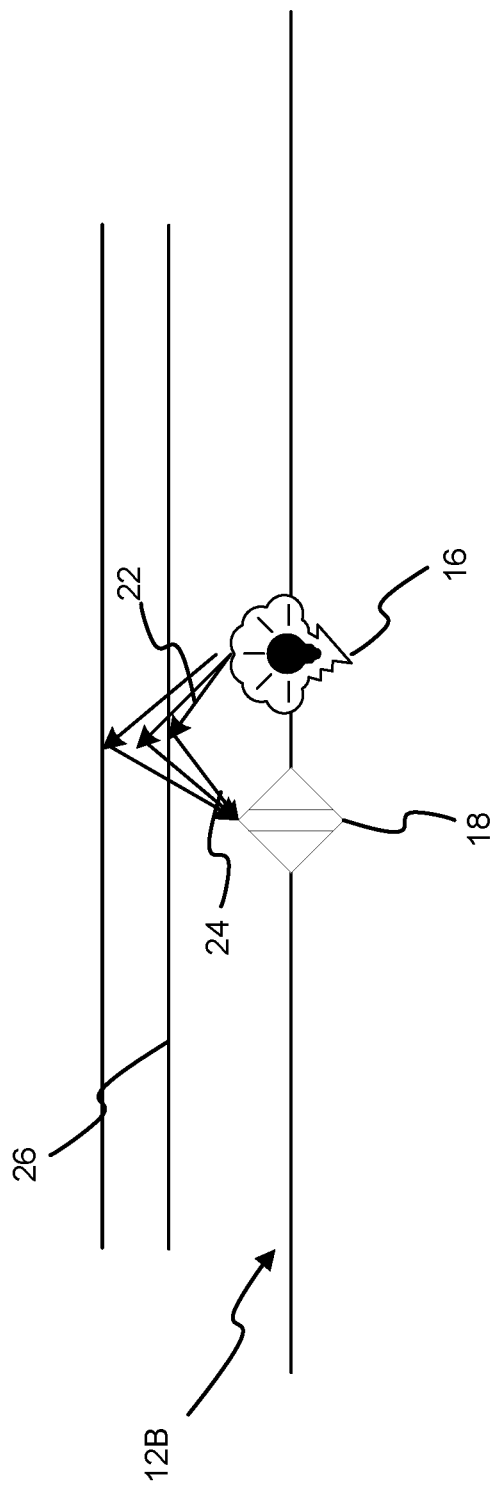
FIG. 3 is a blown-up portion of FIG. 2 illustrating the light source and the light receiver.

FIG. 3 shows an optical source 16 and an optical sensor 18 in close proximity to an ear surface 26. The optical source 16 and/or the optical sensor 18 may even touch the ear surface 26 in certain embodiments. The optical source 16 emits light 22 toward an ear surface 26. If the earpiece 12B is configured to read bone vibration data, then the optical source 16 transmits substantially coherent light 22 or another substantially coherent electromagnetic wave to the optical sensor 18 to use as a reference beam to merge with the reflected light. If the earpiece 12B is configured to determine the direction of the bone vibrations, then the reference beam may be beamed through an acousto-optic modulator to add a small frequency shift to the reference beam, which can be used to help determine a direction of one or more bone vibrations. The light 22 travels through the ear surface 26 and periodically reflects off of bone and tissue within the ear, creating reflected light 24. The reflected light 24 is subsequently received by the optical sensor 18. If the earpiece 12B is configured to read bone vibration measurements, then the reflected light 24 will merge with a reference beam, where the velocity and the displacement information of the bone vibrations can be determined from the frequency shift of the merged wave. The reflected light 24 is then transmitted to one or more processors 20 in order to determine oxygen saturation data and depending on the configuration of one or more processors 20 within the earpiece 12B, bone vibration measurements.

Figure 4:
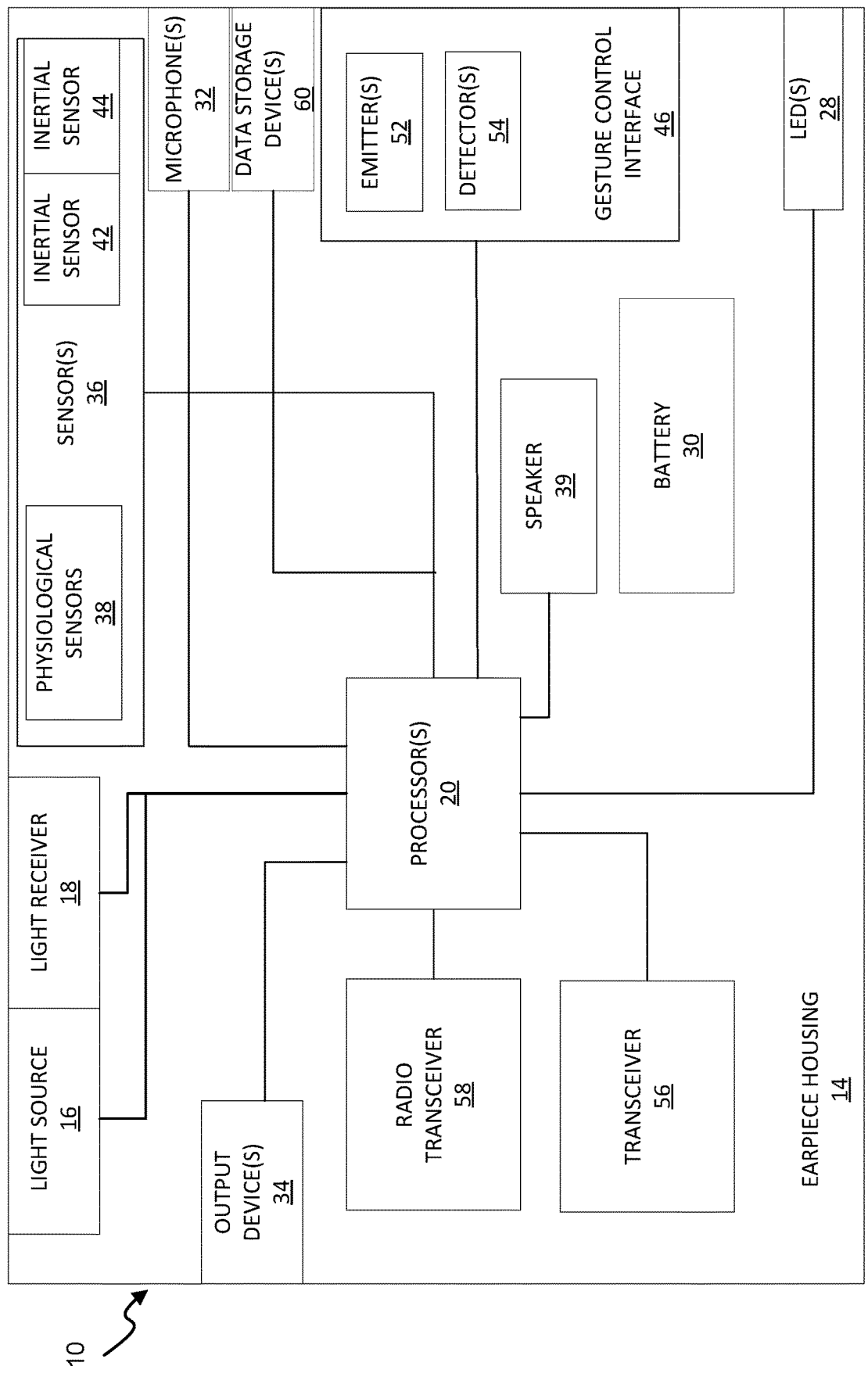
FIG. 4 is a block diagram regarding another embodiment of the system.

FIG. 4 is a block diagram of a system 10 which comprises at least one earpiece 12 with each earpiece 12 further comprising an earpiece housing 14, an optical source 16 operatively connected to the earpiece housing 14, an optical sensor 18 operatively connected to the earpiece housing 14, at least one LED 28 operatively connected to the earpiece housing 14, one or more microphones 32 operatively connected to the earpiece housing 14, one or more output devices 34 such as speakers operatively connected to the earpiece housing 14, at least one sensor 36 operatively connected to the earpiece housing 14 such as physiological sensors 38, or inertial sensors 42, 44, a gesture control interface 46 with at least one emitter 52 and at least one detector 54 operatively connected to the earpiece housing 14, a transceiver 56 disposed within the earpiece 12, a radio transceiver 58 disposed within the earpiece 12, a battery 30 disposed within the earpiece 12, and one or more processors 20 disposed within the earpiece 12. One or more speakers 39 may also be operatively connected to the processor(s) 20.

An optical source 16 is operatively connected to the earpiece housing 14 and configured to emit light toward an ear surface. Other types of electromagnetic radiation capable of reflecting off of human tissue may be substituted for light. The light may be emitted continuously or intermittently in bursts, wherein the bursts may last for any reasonable length of time. If the optical source 16 is configured to measure bone vibrations, the light or electromagnetic source must be substantially coherent in order to accurately measure the bone vibrations. In addition, the distance between the optical source 16 and the ear surface may be fixed or known in order to obtain accurate bone vibration readings, and ideally the optical source 16 and the ear surface touch one another.

An optical sensor 18 is operatively connected to the earpiece housing 14 and configured to receive reflected light from the ear surface which may include pulse oximetry data as well as audio signals. The audio signals may emanate from any source, including the user, a third party, an electronic apparatus, or an entity from nature itself, and may concern music, sounds, instructions, information, or a combination of the aforementioned. The list is non-exclusive and the audio signals do not have to relate to the user or the earpiece 12. The reflected light from the ear surface may be received continuously or discretely by the optical sensor 18 depending on the configuration of the optical source 16. The optical sensor 18, depending on the physical configuration of the earpiece 12, may receive refracted light, or light that has been bent due to travel through human tissue, from the optical source 16 in lieu of reflected light. If one or more processors are configured to calculate bone vibration data, then the optical sensor 18 may receive light directly from the optical source 16 to use as a reference beam in order to accurately measure the velocity of the bone vibrations due to the frequency shift they cause to the reflected light. The reflected light combines with the reference beam in order to create a signal that can be transmitted by the optical sensor 18. The optical sensor 18 may be relatively close to the optical source 16 and the distance between the optical source 16 and the ear surface ideally should be a fixed quantity or the optical source 16 should touch the ear surface. Also, the light or electromagnetic wave should be substantially coherent so that the bone vibration measurements may be accurately determined by one of the processors 20 present within the earpiece 12.

The LEDs 28 affixed to the earpiece housing 14 may be configured to emit light in order to convey information to a user concerning the earpiece 12. The LEDs 28 may be located in any area on the earpiece 12 suitable for viewing by the user or a third party and may consist of as few as one diode which may be provided in combination with a light guide. In addition, the LEDs 28 may be discernable by a human eye or an electronic device and need not have a minimum luminescence.

One or more microphones 32 may be operatively connected to the earpiece housing 14 and may be configured to receive sounds from one or more sources in addition to the optical sensor 18, including the user, a third party, a machine, an animal, another earpiece, another electronic device, or even nature itself. The sounds received by one or more microphones 32 may include a word, combination of words, a sound, combinations of sounds, or any combination of the aforementioned. The sounds may be of any frequency and need not be audible to the user and may be used to reconfigure one or more components of the earpiece 12. One or more of the microphones 32 may be a bone microphone. It is to be understood however, that the earpiece need not include a bone microphone. In addition, the earpiece need not include any microphone at all other than the optical sensor because the optical sensor may be used to sense data including audio signals.

One or more output devices 34 operatively connected to the earpiece housing 14 may be configured to transmit sounds received from one or more microphones 32, the transceiver 56, or the radio transceiver 58 or even a data storage device 60. One or more output devices 34 may transmit information related to the operations of the earpiece 12 or information queried by the user or a third party to outside sources. For example, an output device 34 may transmit a signal related to oxygen saturation levels to an external electronic device. The oxygen saturation levels may be used by a medical professional for diagnostic purposes, a user for technical or personal purposes, or a third party for scientific, technical, or other purposes. An output device 34 may also transmit any audio signals received by the optical sensor 18, which may include music, sounds, instructions, information, commentary, auditory media, or a combination of the aforementioned.

One or more sensors 36 may be operatively connected to the earpiece housing 14 and may be configured to obtain addition oxygen saturation level data that neither the optical source 16 nor the optical sensor 18 are configured for. For example, the microphones 32 may be used to detect vibrations via pressure disturbances in the user's ear canal or one or more inertial sensors 42 and 44 may be used to determine motion data related to the user's head and neck regions to be used to modify one or more readings of the optical sensor 18 or even to ascertain one or more variables of the oxygen saturation level determination. Each sensor 36 may be located anywhere on or within the earpiece housing 14 and need not be in direct contact with either the user or the external environment.

The gesture control interface 46 affixed to the earpiece housing 14 is configured to allow a user additional control over the earpiece 12. The gesture control interface 46 may include at least one emitter 52 and at least one detector 54 to detect gestures from either the user, a third party, an instrument, or a combination of the aforementioned and transmit one or more signals related to one or more gestures to one or more processors 20. The gesture control interface 46 may be implemented using optical emitters and detectors, may be implemented with capacitance sensing, or otherwise. The gestures that may be used with the gesture control interface 46 to control the earpiece 12 include, without limitation, touching, tapping, swiping, use of an instrument, or any combination of the aforementioned gestures. Touching gestures used to control the earpiece 12 may be of any duration and may include the touching of areas that are not part of the gesture control interface 46. Tapping gestures used to control the earpiece 12 may include any number of taps and need not be brief. Swiping gestures used to control the earpiece 12 may include a single swipe, a swipe that changes direction at least once, a swipe with a time delay, a plurality of swipes, or any combination of the aforementioned.

One or more processors 20 are operatively connected to each component within the earpiece 12 and may be configured, in addition to transmitting and receiving signals from either the optical source 16 or the optical sensor 18, to receive signals from one or more microphones 32, one or more sensors 36, the transceiver 56, or the radio transceiver 58. One or more processors may also be configured to use information received from one or more microphones 32, one or more sensors 36, the transceiver 56, or the radio transceiver 58 in addition to information from the optical sensor 18 to assist in the determination of any oxygen saturation level data that may be relevant. One or more processors 20 may be reconfigured by the user or a third party through the use of one or more microphones 32, the gestural control interface 46, or by an electronic signal received from the transceiver 56 or the radio transceiver 58. Reconfigurations may include whether to determine bone vibrations, whether to transmit the oxygen saturation data to an external device, or setting the frequency of optical sensor measurements. The aforementioned list is non-exclusive.

The transceiver 56 disposed within the earpiece 12 may be configured to receive signals from and to transmit signals to a second earpiece of the user if the user is using more than one earpiece. The transceiver 56 may receive or transmit more than one signal simultaneously. The transceiver 56 may be of any number of types including a near field magnetic induction (NFMI) transceiver.

The radio transceiver 58 disposed within the earpiece 12 may be configured to receive signals from external electronic devices and to transmit those signals to one or more processors 20. The external electronic devices the radio transceiver 58 may be configured to receive signals from include Bluetooth devices, mobile devices, desktops, laptops, tablets, modems, routers, communications towers, cameras, watches, third-party earpieces, earpieces, or other electronic devices capable of transmitting or receiving wireless signals. The radio transceiver 58 may receive or transmit more than one signal simultaneously.

The battery 30 may be operatively connected to components within an earpiece 12 to provide power. The battery 30 should provide enough power to operate an earpiece 12 for a reasonable duration of time. The battery 30 may be of any type suitable for powering an earpiece 12. However, the battery 30 need not be present in an earpiece 12. Alternative battery-less power sources, such as thermal harvesters that produce energy from differences between the user's or a third party's skin or internal body temperature and the ambient air, solar apparatuses which generate energy from the photovoltaic effect, or sensors configured to receive energy from radio waves (all of which are operatively connected to one or more earpieces 12) may be used to power the earpiece 12 in lieu of a battery 30.

Figure 5:
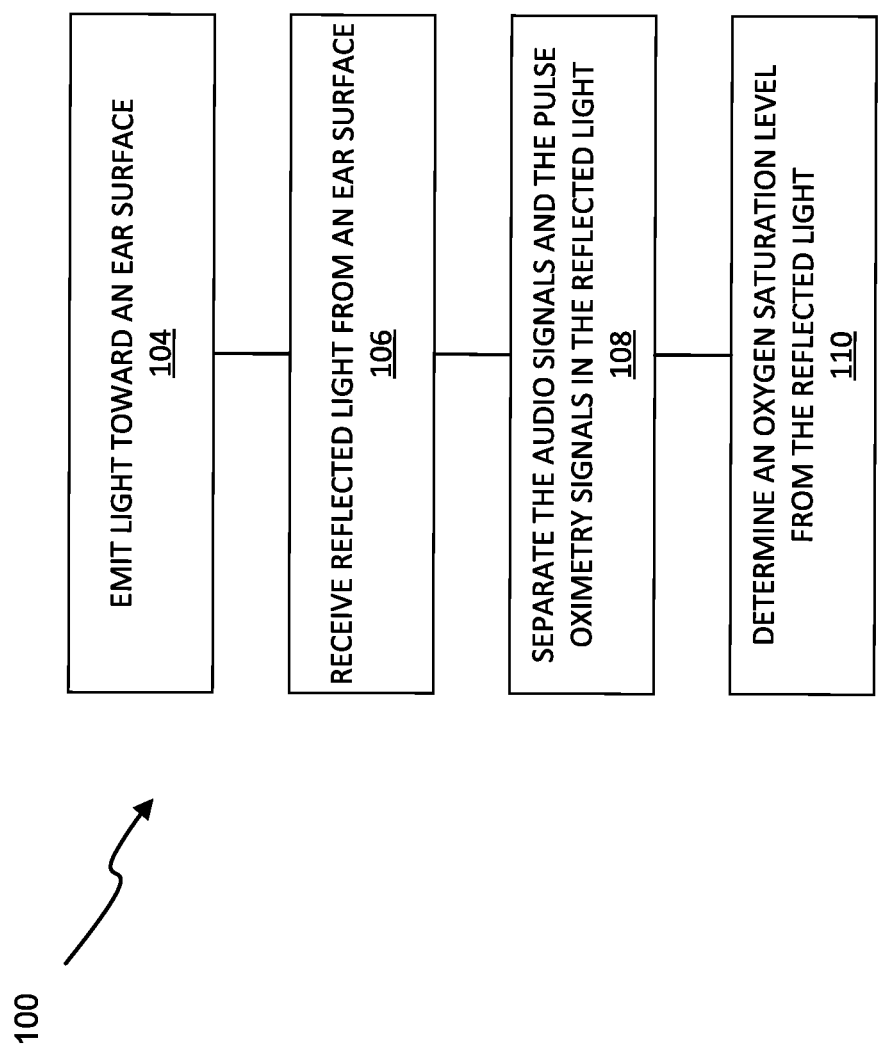
FIG. 5 includes a flowchart of an implementation of a method.

FIG. 5 illustrates one embodiment of the method 100. In step 104, an earpiece emits light toward an ear surface. Any type of electromagnetic wave may be substituted for light as long as it is capable or reflecting off of human tissue, and the ear surface may be any surface suitable of reflecting electromagnetic radiation and may be on the outside or the inside of the ear. The light may be emitted intermittently in pulses or continuously at the ear surface. In step 106, an optical sensor receives both audio signals and pulse oximetry signals within the reflected light from the ear surface. The audio signals may originate from the user, a third party, an electronic apparatus, an animal, or even nature itself, and the audio signals may include more than one type of audio signal. The audio signals also do not need to be audible to the user, and may be used to modify or reconfigure the earpiece or a component within the earpiece. The reflected light, like the light, may be substituted with any type of electromagnetic wave capable of reflecting off of human tissue and does not need to be the same intensity as the light. In step 108, one or more processors separates the audio signals and the pulse oximetry signals from the reflected light. In step 110, one or more processors determines an oxygen saturation level from the pulse oximetry signals in the reflected light. A processor may use an algorithm stored within the processor itself or use an algorithm stored within a data storage device operatively connected to a processor. The oxygen saturation may also be provided to the user or a third party.

Figure 6:
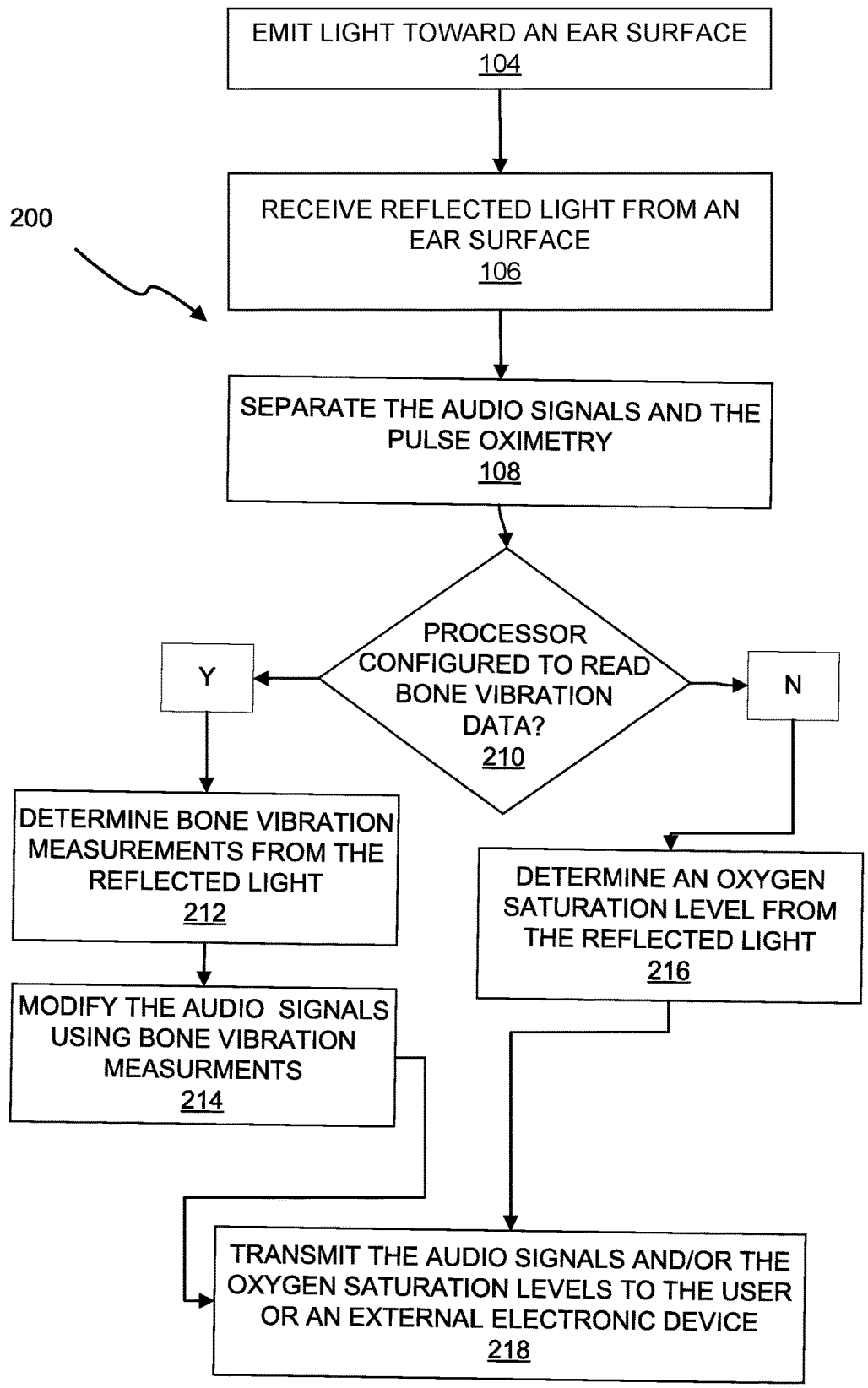
FIG. 6 includes a flowchart of another implementation of the method

FIG. 6 illustrates a second embodiment of the method 200. The first steps are identical to the first steps of FIG. 5, but after separating the audio signals and the pulse oximetry signals from the reflected light, one or more processors, in step 210, checks to see if they are configured to determine bone vibration measurements from the reflected light. If so, then, in step 212, one or more processors determine bone vibration measurements from the reflected light. One or more processors involved in determining bone vibration measurements may use an algorithm stored within one of the processors or an algorithm stored within one or more data storage devices operatively connected to one of the processors, and the processors involved in the determination do not need to consider all of the data related to the reflected light. Any number of algorithms for extracting voice input from bone vibrations may be used including any number of speech recognition algorithms including hidden Markov models, dynamic time warping, neural networks, genetic algorithms or other methods. The voice input may contain keywords or voice commands of the user of the wireless earpiece. The reflected light data may be received continuously or intermittently in bursts of varying length. In step 214, the bone vibration measurements are used to modify the audio signals so as to maintain the audio signals original fidelity. The audio signals may not need modification, but de minimis modifications will have no effect on the audio signals fidelity. If none of the processors are configured to read bone vibration data, then in step 216, one or more processors determines an oxygen saturation level from the reflected light. Like the determination of the bone vibration measurements, a processor involved in the oxygen saturation level determination may use an algorithm stored within one of the processors or an algorithm stored within one or more data storage devices operatively connected to a processor, and the processor does not need to consider all of the reflected light data. Regardless of whether one or more of the processors was configured to determine bone vibration data in step 210, in step 218, the oxygen saturation levels and/or the audio signals are transmitted to the user or an external electronic device. The external electronic device may be a smartphone, tablet, watch, modem, router, communications tower, or a medical device, wherein the medical device is used for medical diagnosis or treatment.

Therefore, various methods, systems, and apparatus have been shown and described. Although specific embodiments are set forth herein, the present invention contemplates numerous options, variations, and alternatives including variations in type of optical source and optical sensor,

What is claimed is:

1. A system comprising:
    at least one earpiece, wherein each earpiece comprises an earpiece housing;
    an optical source operatively connected to the earpiece housing, wherein the optical source is configured to emit light toward an ear surface;
    an optical sensor operatively connected to the earpiece housing, wherein the optical sensor is configured to receive reflected light from the ear surface; and
    at least one processor disposed within at least one earpiece and operatively connected to the optical source and the optical sensor, wherein the at least one processor is configured to separate the pulse oximetry signals from the audio signals in the reflected light detected by the optical sensor and use the audio signals to receive voice input from a user wearing the at least one earpiece.

2. The system of claim 1 wherein the at least one processor is further configured to determine an oxygen saturation level from the pulse oximetry signals.

3. The system of claim 1 wherein the at least one processor applies a filter to separate the pulse oximetry signals from the audio signals, the audio signals centered at frequency higher than the pulse oximetry signals.

4. The system of claim 1 wherein the at least one earpiece comprises a set of earpieces.

5. The system of claim 1 wherein the optical source is a laser.

6. The system of claim 1 wherein the ear surface comprises an outer ear surface.

7. The system of claim 1 wherein the ear surface comprises an inner ear surface.

8. A method comprising:
emitting, via an optical source of a wireless earpiece, light toward an ear surface;
receiving, via an optical sensor of the wireless earpiece, a reflected light signal from the ear surface;
separating, via at least one processor of the wireless earpiece, audio signals from pulse oximetry signals within the reflected light signal;
determining, via the at least one processor of the wireless earpiece, an oxygen saturation level from the reflected light;
calculating bone vibration measurements via the at least one processor of the wireless earpiece using the audio signals; and
interpreting the bone vibration measurements to determine voice input of a user of the wireless earpiece.

9. The method of claim 8 wherein the optical source is a laser.

10. The method of claim 8 wherein the ear surface comprises an outer ear surface.

11. The method of claim 8 wherein the ear surface comprises an inner ear surface.

12. The method of claim 8 further comprising reconfiguring the at least one processor using the voice input.

\* \* \* \* \*